US011654041B2

(12) United States Patent
Norfleet (10) Patent No.: US 11,654,041 B2
(45) Date of Patent: May 23, 2023

(54) SYSTEM FOR COVERING AND VISUALLY DISTINGUISHING AN INJURED LIMB

(71) Applicant: Emily M Norfleet, Chino, CA (US)

(72) Inventor: Emily M Norfleet, Chino, CA (US)

( * ) Notice: Subject to any disclaimer, the term of this patent is extended or adjusted under 35 U.S.C. 154(b) by 45 days.

(21) Appl. No.: 17/486,872

(22) Filed: Sep. 27, 2021

(65) Prior Publication Data

US 2022/0096261 A1 Mar. 31, 2022

Related U.S. Application Data

(60) Provisional application No. 63/083,397, filed on Sep. 25, 2020.

(51) Int. Cl.
*A61F 5/37* (2006.01)
*A61B 90/94* (2016.01)

(52) U.S. Cl.
CPC ............ *A61F 5/3738* (2013.01); *A61B 90/94* (2016.02)

(58) Field of Classification Search
CPC .... A61F 5/3723; A61F 5/3738; A61F 5/3746; A61F 5/3753; A61B 90/90; A61B 90/94
See application file for complete search history.

(56) References Cited

U.S. PATENT DOCUMENTS

2004/0215119 A1\* 10/2004 Avon .................... A61F 5/3738
602/4
2020/0022861 A1\* 1/2020 Miller .................. A61G 13/125

\* cited by examiner

*Primary Examiner* — Camtu T Nguyen (57) ABSTRACT

A system for covering and visually distinguishing an injured limb is used to enclose and visually indicate a physical injury to prevent exacerbating said injury through unwanted contact. Additionally, wound recovery times may be shortened by insulating and protecting an injured limb throughout a convalescence period. The present invention utilizes a medical brace enclosed in a covering textile, with at least one fastener securing the covering textile about the medical brace and a user's injured limb. At least one visual indicium is mounted onto the covering textile to provide direct indication to the nature of injury. The visual indicium displayed across the covering textile will ideally encourage surrounding persons to avoid physical contact with the user, thereby preventing any undue discomfort caused by bumping or jostling the injured limb.

15 Claims, 8 Drawing Sheets

Figure 7:
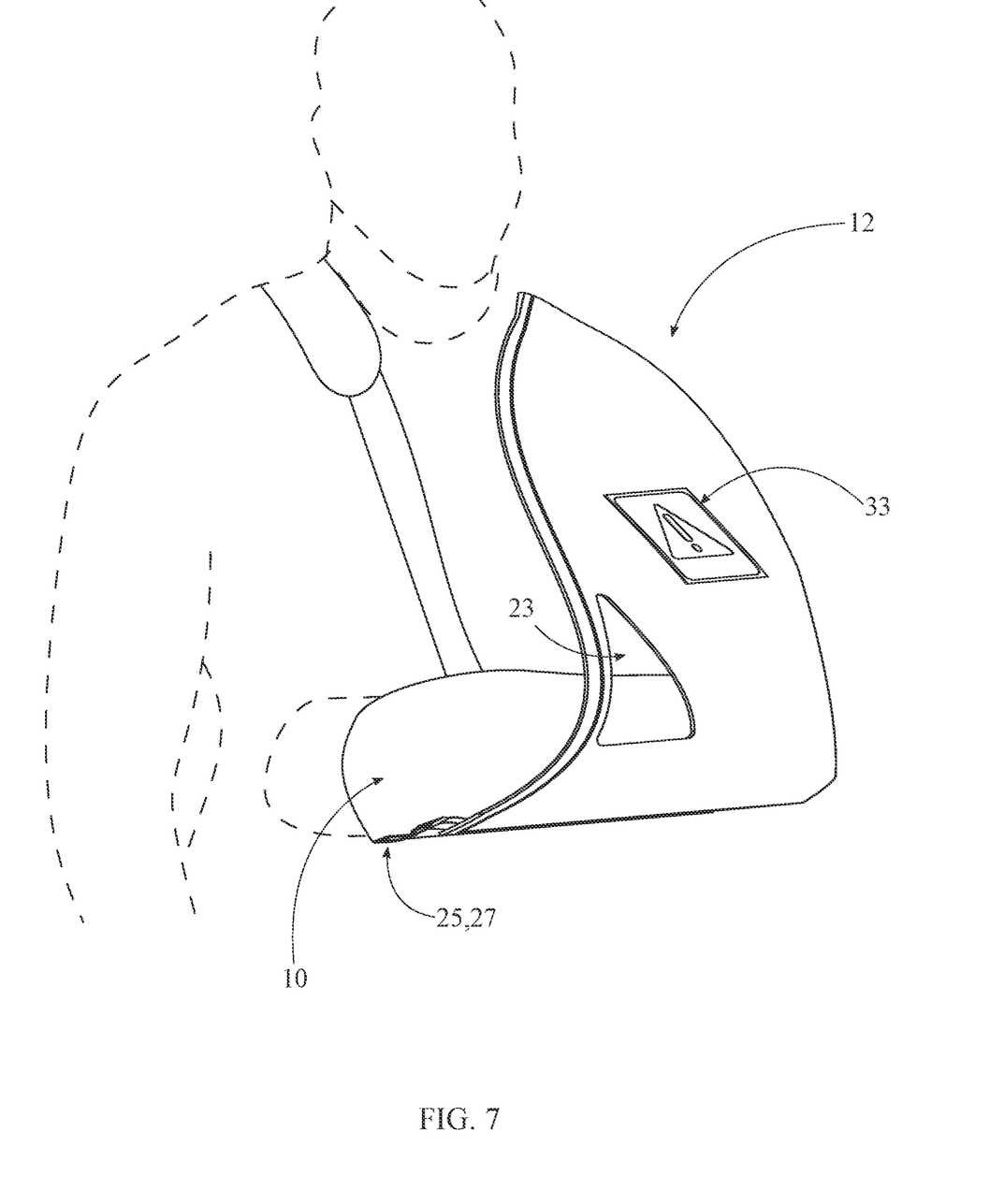

SYSTEM FOR COVERING AND VISUALLY DISTINGUISHING AN INJURED LIMB

The current application claims a priority to the U.S. Provisional Patent application Ser. No. 63/083,397 filed on Sep. 25, 2020. The current application is filed on Sep. 27, 2021 while Sep. 25, 2021 and Sep. 26, 2021 were on a weekend.

FIELD OF THE INVENTION

The present invention generally relates to medical care. More specifically, the present invention relates to a cover that can be used to provide local hypothermic effects at the zone of injury on the body of a victim who has sustained various injuries. The present invention also serves as a visual warning against unwanted contact to sensitive, injured regions.

BACKGROUND OF THE INVENTION

A covering device that can be conveniently used to protect patients' injured body parts is in demand.

Medical covers or blankets provide comfort for patients who are experiencing trauma, and medical professionals can use them for various reasons, whether to prevent shock and rapid cooling, reduce hypothermia risks, or avoid wound complications.

In addition, medical covers and blankets can be used to assist with patient positioning by providing extra padding or can be rolled up to provide support.

For emergency medical care, surgery, and resuscitation, it is sometimes necessary to keep a patient's body warm, especially during emergencies that involve major blood loss, amid winter temperatures, or in water.

Because the human body uses blood to control the distribution of heat internally, low body temperatures can cause hypothermia with time, particularly when water and blood loss are involved: water conducts heat far more quickly than air does, and in a person who is wet while out of water, evaporative cooling can drain even more heat, especially in windy conditions.

Traditional casting applications for fractures may also use various covers and cloth strips to immobilize body parts during hardening of a cast, but many such covering mechanisms have their own drawbacks, including treatment-related problems and materials-related problems. Often such covers are difficult to detach after having been wrapped around injured parts, are difficult to use, or are uncomfortable when worn.

Some covers are made of materials that are not intended to provide local hypothermic effects at the zone of a traumatic injury to a patient's body and are not designed for use in medical care facilities, whether ambulances, operating rooms, or intensive care units. Thus, there is a need to develop a device that solves these problems.

The present invention is intended to address problems associated with and/or otherwise improve on conventional devices through an innovative covering device that is designed to provide a convenient means of wrapping local injuries and providing local hypothermic effects while incorporating other problem-solving features.

BRIEF DESCRIPTION OF THE DRAWINGS

FIG. 1 is an illustration of one embodiment of the present invention, specifically an embodiment configured for use in combination with a shoulder sling.

FIG. 2 is a partially exploded view thereof, wherein internal components and regions of the present invention are indicated and rendered in broken-line.

FIG. 3 is a detail view of area 3-3 in FIG. 2.

FIG. 4 is a detail view of area 4-4 in FIG. 2.

FIG. 5 is a perspective view of one embodiment of a covering textile, wherein the covering textile is delaminated to shown construction and layering.

FIG. 6 is a detail view of area 6-6 in FIG. 5.

FIG. 7 is a frontal perspective view of the present invention in-use by a patient, wherein the patient silhouette is rendered in broken-line.

FIG. 8 is a rear perspective view of the present invention in-use by a patient, wherein the patient silhouette is rendered in broken-line.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

In reference to FIG. 1 through 8, the present invention is a system for covering and visually distinguishing an injured limb comprising a medical brace 10, a covering textile 12, at least one fastener 25, and at least one visual indicium 33. The present invention is directed primarily towards modifying and improving existing medical slings, braces, immobilization harnesses, and other wearable medical devices with a distinctive covering. This arrangement ideally prevents unaware individuals from bumping into or otherwise disturbing an injured user by clearly identifying an injured or sensitive body part.

The medical brace 10 broadly encompasses any type of wearable or applique medical support as may be readily understood by any reasonably skilled individual. This categorization includes, but is not limited to, shoulder immobilizers, elbow immobilizers, rotator cuff supports, shoulder braces, compression sleeves, humeral splints, clavicle immobilizers, offset arm slings, knee braces, wrist splints, and other comparable medical devices. The components of the present invention are ideally configured, by manufacture or modification, to conform to all embodiments of the medical brace 10 without departing from the original spirit and scope of the present invention.

The covering textile 12 constitutes a flexible polyester fabric ideally suitable for extended contact against a user's skin. As shown in FIG. 1, the covering textile 12 comprises an exterior surface 13 and an interior surface 14. The exterior surface 13 is ideally a durable material suitable for extended exposure to moisture, abrasion, debris, or other hazards that may compromise the covering textile 12. Conversely, the interior surface 14 ideally comprises a compressible, breathable fabric configured to enclose and support an injured limb without causing undue discomfort to a user. Accordingly, the medical brace 10 is enclosed within the covering textile 12 as shown in FIG. 7. The medical brace 10 is positioned against the interior surface 14, including any uncovered portions of a user's body adjacent to the injured limb. This arrangement ensures that the portion of a user's body requiring the greatest protection, i.e., the portion of the body supported by the medical brace 10, is fully engaged to the covering textile 12. Opposite to the interior surface 14, the exterior surface 13 will naturally be disposed outward from the medical brace 10 to present the most durable portion of the covering textile 12 against any external hazards.

Figure 8:
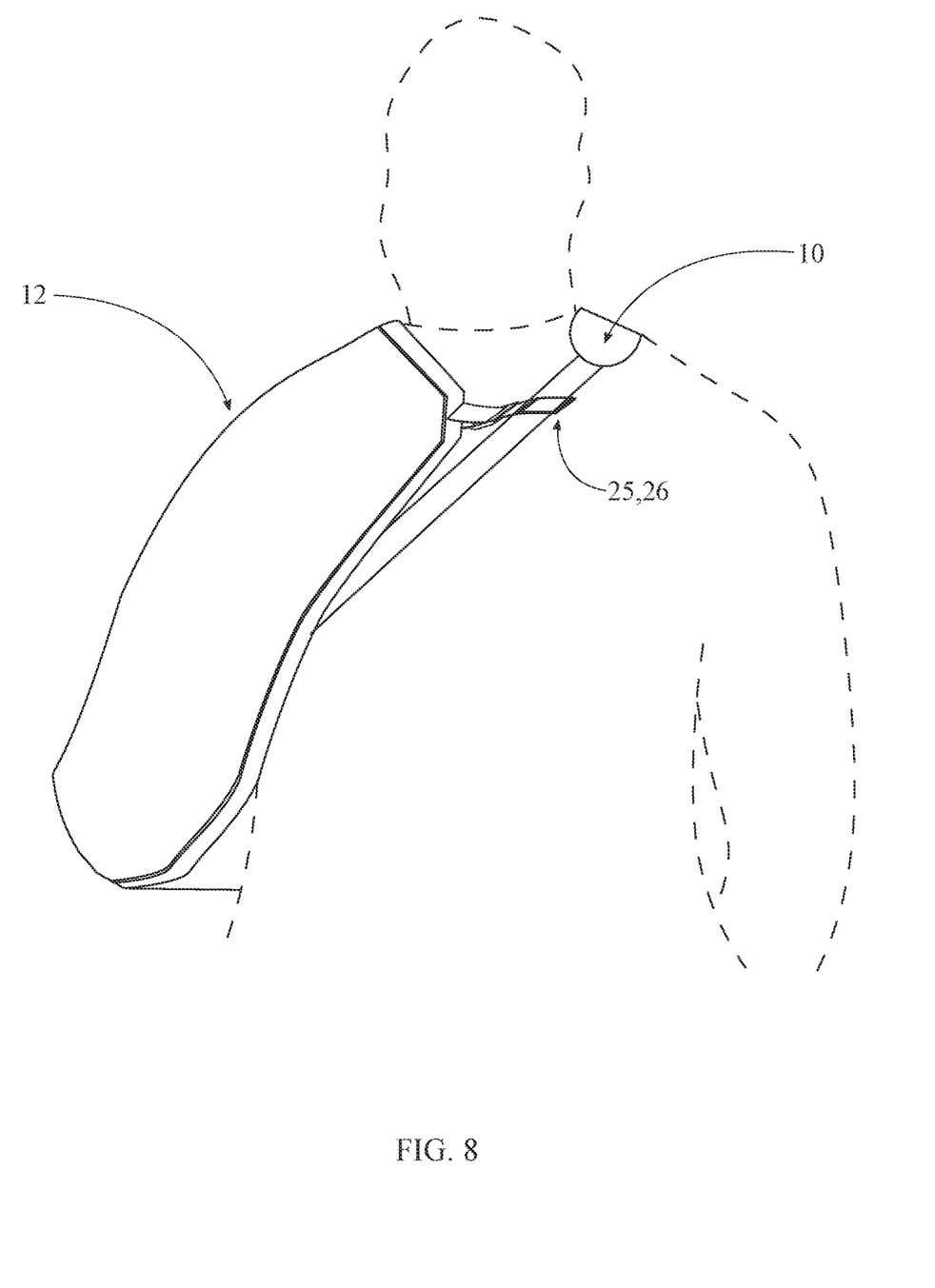

As shown in FIGS. 7 and 8, the covering textile 12 is removably attached onto the medical brace 10 by the at least one fastener 25. This attachment prevents the covering textile 12 from shifting or displacing from the medical brace 10 once affixed and is ideally adjustable to fit any embodiment of the medical brace 10 or any bodily dimensions of a given user. Accordingly, the at least one fastener 25 broadly defines any form of mechanical, magnetic, or adhesive connector as may be suitable for any given embodiment of medical brace 10. Universal embodiments may constitute a closeable loop or strap of sufficient length to fully enclose the medical brace 10. Possible alternate embodiments may utilize proprietary connectors configured to attach to corresponding hardpoint of the medical brace 10, inducing at least one instance wherein the medical brace 10 is manufactured or modified to accept the at least one fastener 25 as a dedicated component of the present invention.

Figure 2:
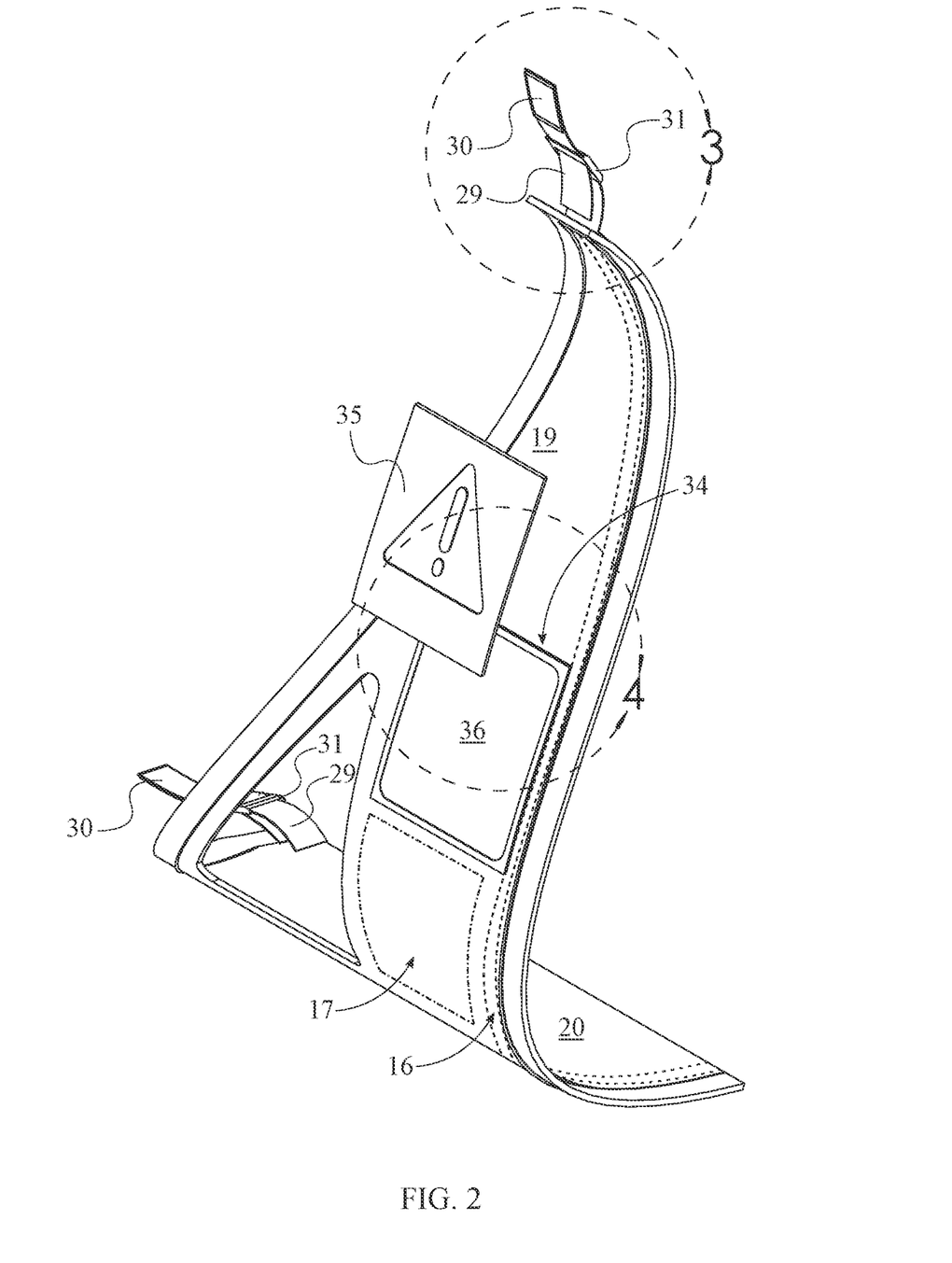

The at least one visual indicium 33 is mounted onto the exterior surface 13 of the covering textile 12 as shown in FIG. 2. The visual indicium 33 constitutes any distinct marking, insignia, color pattern, retroreflective surface, or other visible warning to casual observers or passersby that the user's limb beneath the covering textile 12 is potentially sensitive or delicate. In a preferred embodiment, the at least one visual indicium 33 will prevent anybody from unwittingly bumping into the user and causing undue discomfort to an injured limb. In another embodiment, the at least one visual indicium 33 may be used to relay pertinent medical information to first responders and medical personnel, e.g., that the user is on certain medications, has suffered specified injuries, or has implanted metallic reinforcements beneath the medical brace 10. In general application, the visual indicium 33 serves as a user-configurable notice to the public that the user of the present invention is recovering from an injury and may require special considerations to avoid exacerbating said injury.

Figure 1:
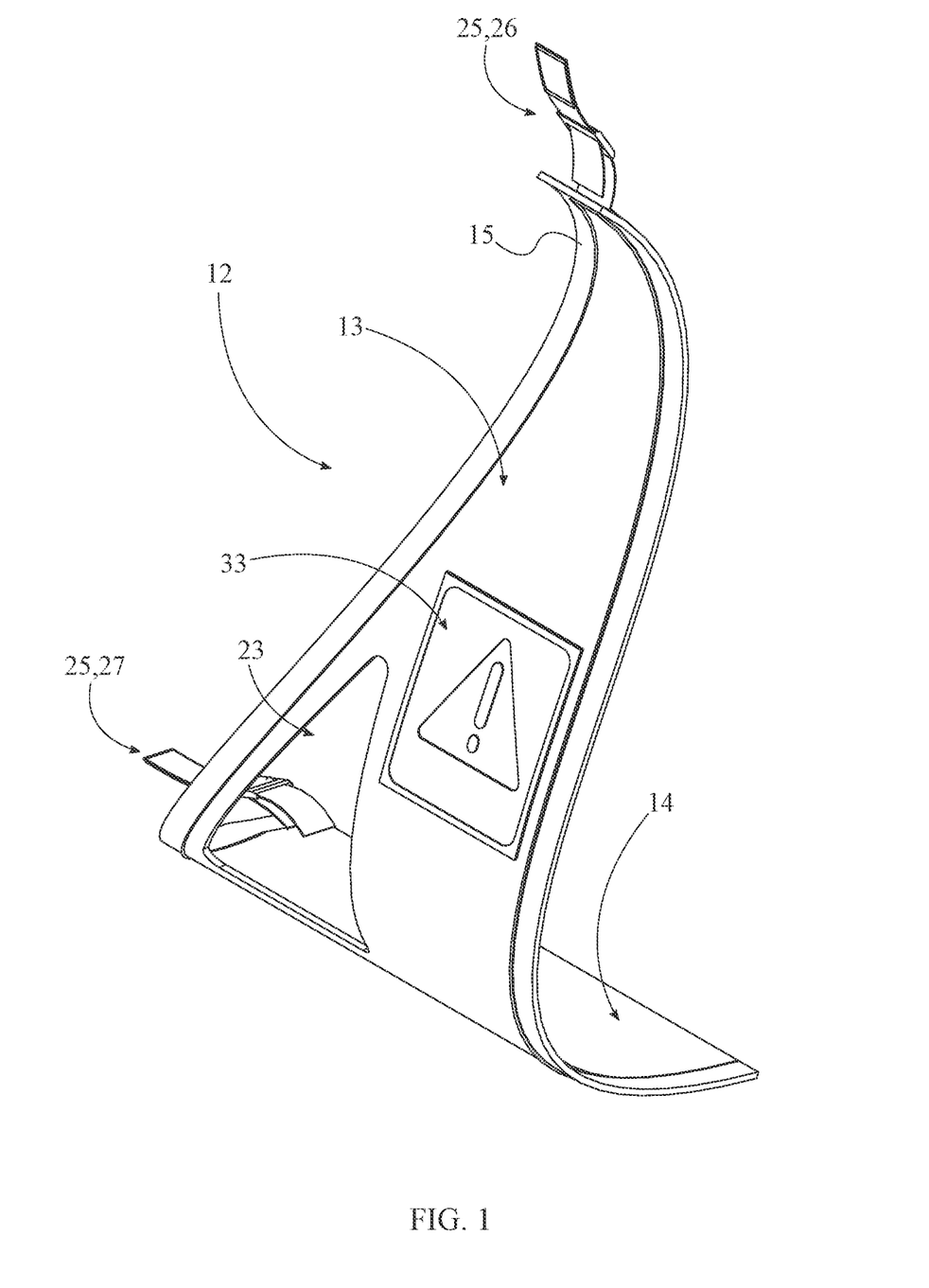

In reference to FIGS. 1 and 2, the at least one fastener 25 is a first fastener 26 and a second fastener 27. The first fastener 26 and the second fastener 27 ideally define similar, universal connection devices as previously outlined, but may also be configured as dissimilar connectors suitable for attaching to, e.g., a user's arm and the medical brace 10 respectively. The covering textile 12 also further comprises a skirt edge 15 extending between the exterior surface 13 and the interior surface 14, wherein the skirt edge 15 extends outwards from the exterior surface 13 to conceal and protect the at least one fastener 25 in a preferred configuration. More specifically, a user attaches the first fastener 26 between the covering textile 12 and the medical brace 10, such that the covering textile 12 wraps around or across a user's body to enclose the medical brace 10 as previously specified. The second fastener 27 is further attached to the medical brace 10 opposite the first fastener 26, fixing the covering textile 12 in position across the user's body. Accordingly, the first fastener 26 is mounted to the interior surface 14 of the covering textile 12 adjacent to the skirt edge 15. The second fastener 27 is also mounted to the interior surface 14 of the covering textile 12 adjacent to the skirt edge 15, opposite the first fastener 26 across the covering textile 12.

Figure 3:
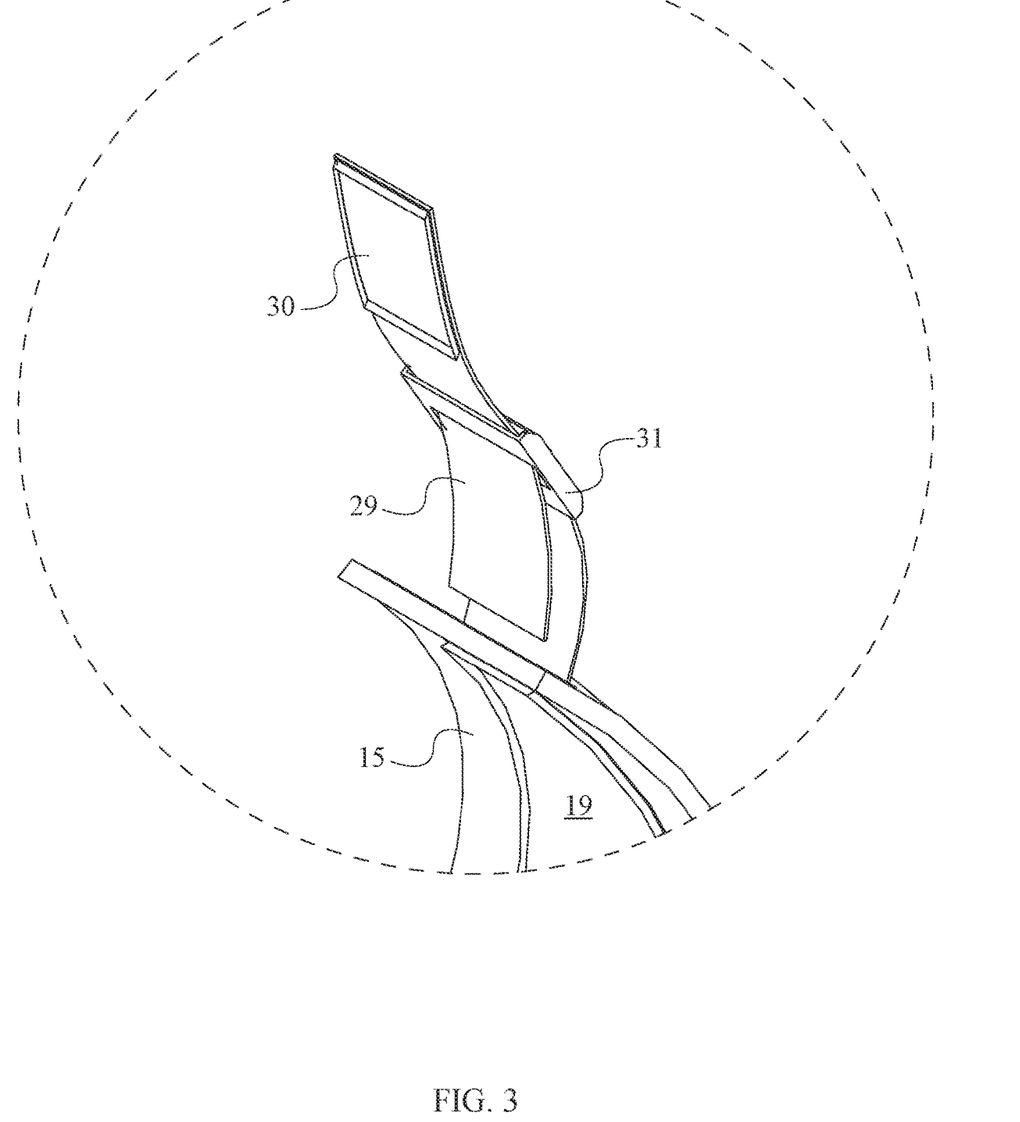
Figure 4:
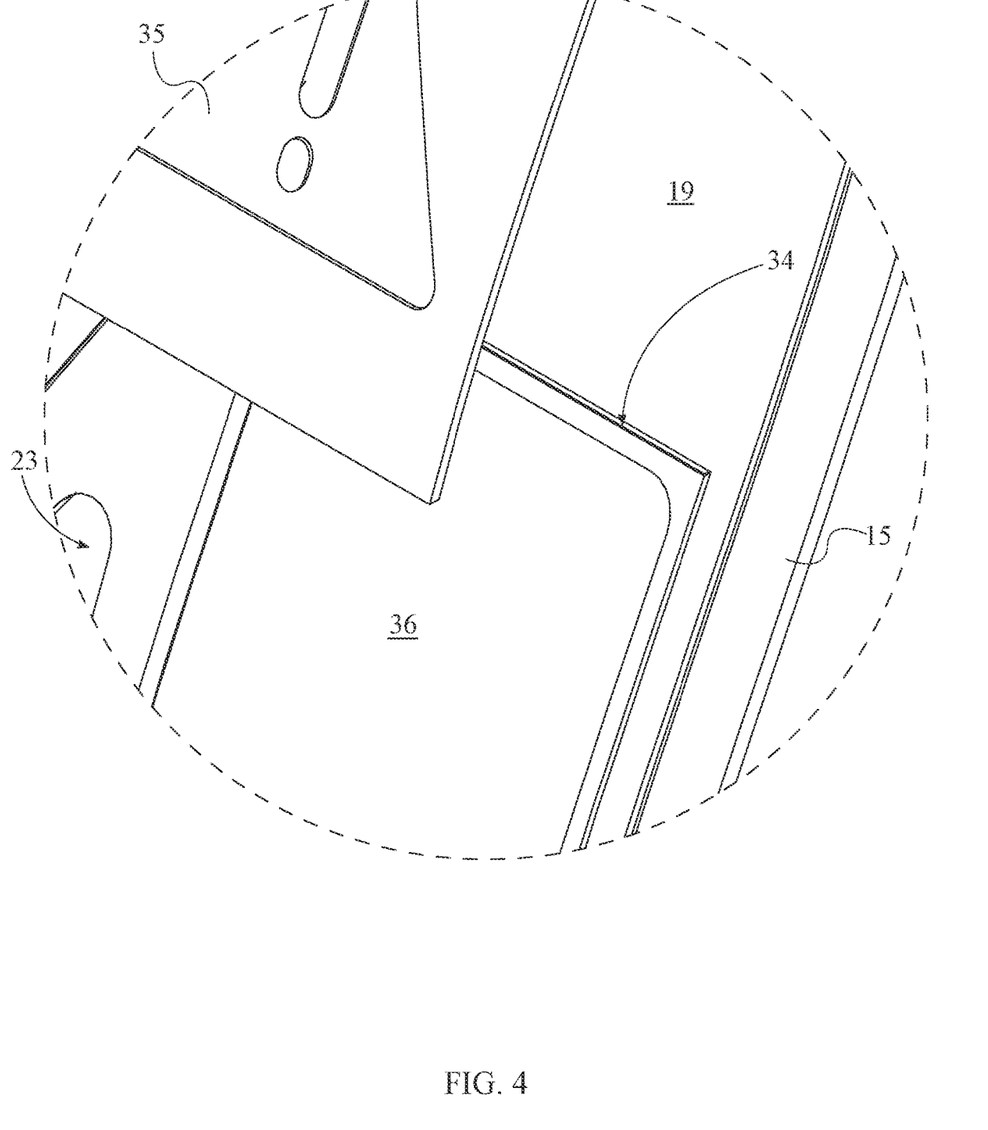

In another embodiment, each of the at least one fastener 25 further comprises a length of webbing 29, an engagement device 30, and length-adjustment mechanism 31 as shown in FIG. 3. The length of webbing 29 is terminally mounted to the covering textile 12 and the engagement device 30 is terminally mounted to the length of webbing 29, opposite the covering textile 12. The length of webbing 29 defines an elongate tensile strap, cord, or leash of suitable dimensions to extend between the covering textile 12 and the medical brace 10 in any embodiment thereof. The engagement device 30 broadly refers to any releasable fastener or fastener-like component compatible with any portion of the medical brace 10. Ideally the engagement device 30 constitutes a paired set of hook-and-loop fasteners disposed between the medical brace 10 and the length of webbing 29, but this embodiment should not be considered limiting to the overall scope of the present invention across all conceivable embodiments. Further, the length-adjustment mechanism 31 is mounted to the length of webbing 29 between the covering textile 12 and the engagement device 30. The length-adjustment mechanism 31 is configured to moderate the overall length of the at least one fastener 25 by selectably retaining the length of webbing 29, whereby the covering textile 12 may be tightened down over the medical brace 10. The length-adjustment mechanism 31 is preferably a slip buckle wound into the length of webbing 29 but may also constitute a spring-loaded clasp in at least one alternate embodiment.

The present invention may further comprise at least one aperture 23 as shown in FIG. 7. The at least one aperture 23 traverses the covering textile 12 between the interior surface 14 and the exterior surface 13, thereby forming an unobstructed path through the covering textile 12 in a variety of conceivable embodiments. In one embodiment, the aperture 23 is positioned to enable the unrestricted movement of a limb within the covering textile 12, whereby the covering textile 12 is contoured for application to a specific subset of medical brace 10 in at least one embodiment. The at least one aperture 23 may also be positioned to permit the covering textile 12 to be mounted around a body part prior to attachment with the at least one fastener 25. The at least one aperture 23 may also be configured to increase airflow across the medical brace 10 within the covering textile 12. This configuration will ideally minimize any discomfort during extended use of the present invention in warmer climates by releasing body heat trapped within the covering textile 12.

It is generally contemplated that the presentation and coloration of the covering textile 12 and the at least one visual indicium 33 serves as an effective visual indicator of an injured or sensitive limb. However, a user may also indicate the nature of an injury and any medical information related thereto using interchangeable visible markers. In one embodiment, the at least one visual indicium 33 comprises a retainer pocket 34, a placard insert, and a transparent section 36. The retainer pocket 34 is mounted to the exterior surface 13 of the cover member with the placard insert 35 positioned into the retainer pocket 34. In turn, the transparent section 36 is mounted to the retainer pocket 34 and positioned over the placard insert. The placard insert 35 preferably contains any immediately recognizable visual warnings, identifying information, or pertinent medical indications that the user chooses to relay to the public. The retainer pocket 34 defines any attachable or moldable feature of the exterior surface 13 suitable for containing the placard insert, wherein the retainer pocket 34 constitutes suitable dimensions and retentive features to hold the placard insert 35 therein. Further, the transparent section 36 defines a portion of feature of the retainer pocket 34 of suitable dimensions to enable a casual observer to recognize and read the placard insert 35 within the retainer pocket 34.

Figure 5:
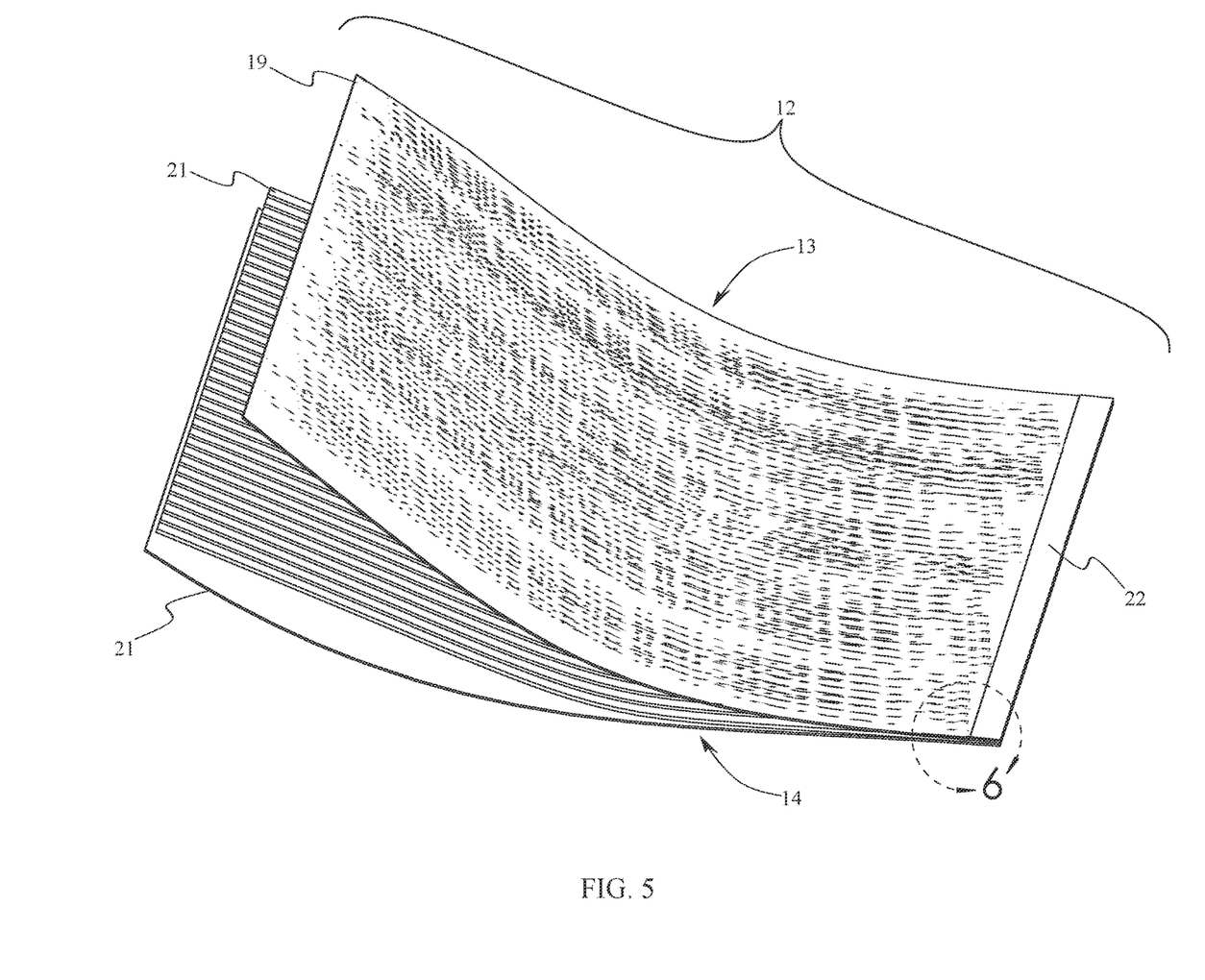
Figure 6:
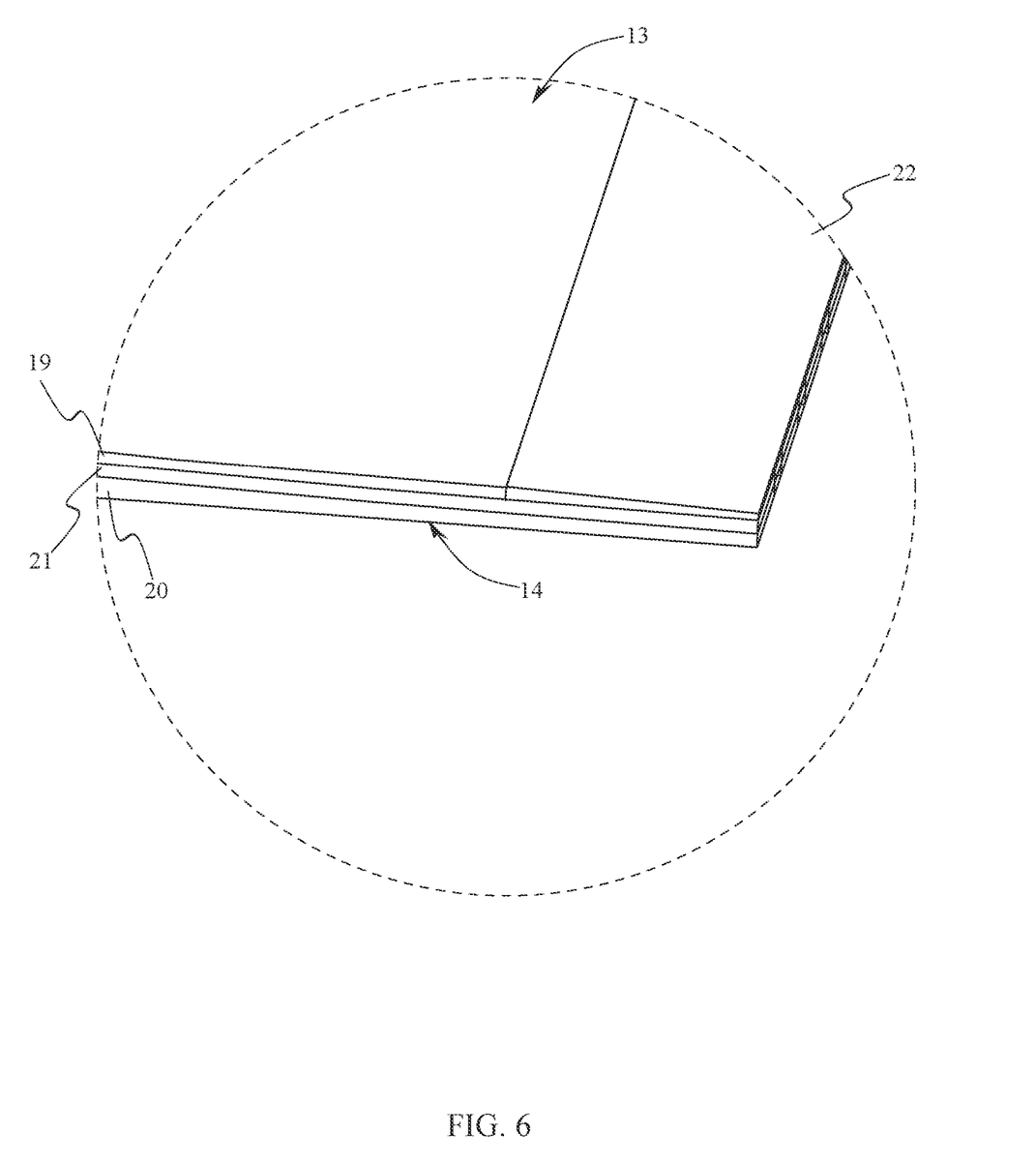

The variability of the covering textile 12 across all conceivable embodiments enables the present invention to be configured for a virtually unlimited range of climates by interchanging the constituent materials thereof. Colder weather may inform the construction of the covering textile 12 to include insulated materials and waterproof coatings, whereas warmer climates may require that an embodiment maximizes the use of sheer fabrics and open airflow across the medical brace 10. Accordingly, the covering textile 12 further comprises a first textile 19, a second textile 20, an interstitial layer 21, and an edge seam 22 in at least one embodiment. As shown in FIGS. 5 and 6, the edge seam 22 is perimetrically mounted between the first textile 19 and the second textile 20, ideally forming a permanent material bond between the disparate materials of the first textile 19 and the second textile 20. The interstitial layer 21 is delineated by the edge seam 22 and positioned between the first textile 19 and the second textile 20. The first textile 19 and the second textile 20 constitute any set of dislike materials as may be commonly used in the garment industry including any type of woven, melt-blown, or laminated materials commonly used in the field. The interstitial layer 21 is preferably formed from a variable density material configured by manufacture for a target climate. For example, the interstitial layer 21 may be configured for insulating the user against colder weather in one embodiment or may be configured to resist heat buildup from intense direct sunlight and high humidity in another embodiment. General recombinations and variations of the materials comprising the first textile 19, the second textile 20, and the interstitial layer 21 to increase suitability for target environments are generally considered to fall within the original spirit and scope of the present invention.

Although the medical brace 10 is generally considered to be self-supporting, it is recognized that the covering textile 12 is uniquely positioned to lend additional positional support to an injured limb by virtue of fully enclosing the medical brace 10. To provide additional functionality as a secondary support to the medical brace 10, the covering textile 12 further comprises at least one inelastic section 16 mounted between the exterior surface 13 and the interior surface 14. The inelastic section 16 provides an integral strap or leash for the medical brace 10 formed into the covering textile 12, arranged in support of extant portions of the medical brace 10 as shown in FIG. 2. In another embodiment, the inelastic section 16 may be disposed perpendicular to the normal range of motion of a limb, thereby preventing the hyperextension of a supported joint by halting the travel of the medical brace 10 engaged thereto. The inelastic section 16 is terminally positioned adjacent to the at least one fastener 25, wherein the inelastic section 16 is configured to positionally support the medical brace 10.

In regular use, the covering textile 12 normally contacts both the medical brace 10 and some portion of a user's skin directly. The medical brace 10 is generally constructed of an externally durable material and requires no special consideration, but long-term contact against an impermeable, coarse embodiment of the covering textile 12 will cause chafing and general discomfort for a user. Therefore, the covering textile 12 further comprises at least one vapor-permeable section 17 as shown in the embodiment illustrated in FIG. 2. The vapor-permeable section 17 ideally constitutes a breathable, contact-safe portion of the covering textile 12 configured and positioned for direct contact against any portion of the user's body not covered by the medical brace 10. Accordingly, the vapor-permeable section 17 is mounted between the exterior surface 13 and the interior surface 14, wherein the at least one vapor-permeable section 17 is positioned offset from the medical brace 10.

Although the invention has been explained in relation to its preferred embodiment, it is to be understood that many other possible modifications and variations can be made without departing from the spirit and scope of the invention as hereinafter claimed.

What is claimed is:

1. A system for covering and visually distinguishing an injured limb comprising:
    a medical brace;
    a covering textile;
    at least one fastener;
    at least one visual indicium;
    the covering textile comprising an exterior surface and an interior surface;
    the medical brace being enclosed within the covering textile;
    the medical brace being positioned against the interior surface;
    the covering textile being removably attached onto the medical brace by the at least one fastener; and
    the at least one visual indicium being mounted onto the exterior surface.

2. The system for covering and visually distinguishing an injured limb as claimed in claim 1 comprising:
    the at least one fastener being a first fastener and a second fastener;
    the covering textile further comprising a skirt edge extending between the exterior surface and the interior surface;
    the first fastener being mounted to the interior surface of the covering textile adjacent to the skirt edge; and
    the second fastener being mounted to the interior surface of the covering textile adjacent to the skirt edge, opposite the first fastener across the covering textile.

3. The system for covering and visually distinguishing an injured limb as claimed in claim 1 comprising:
    each of the at least one fastener further comprising a length of webbing, an engagement device, and length-adjustment mechanism;
    the length of webbing being terminally mounted to the covering textile;
    the engagement device being terminally mounted to the length of webbing, opposite the covering textile; and
    the length-adjustment mechanism being mounted to the length of webbing between the covering textile and the engagement device.

4. The system for covering and visually distinguishing an injured limb as claimed in claim 1 comprising:
    at least one aperture; and
    the at least one aperture traversing the covering textile between the interior surface and the exterior surface.

5. The system for covering and visually distinguishing an injured limb as claimed in claim 1 comprising:
    the at least one visual indicium comprising a retainer pocket, a placard insert, and a transparent section;

the retainer pocket being mounted to the exterior surface of the covering textile;
the placard insert being positioned into the retainer pocket; and
the transparent section being mounted to the retainer pocket and positioned over the placard insert.

6. The system for covering and visually distinguishing an injured limb as claimed in claim 1 comprising:
the covering textile further comprising a first textile, a second textile, an interstitial layer, and an edge seam;
the edge seam being perimetrically mounted between the first textile and the second textile; and
the interstitial layer being delineated by the edge seam and positioned between the first textile and the second textile.

7. The system for covering and visually distinguishing an injured limb as claimed in claim 1 comprising:
the covering textile further comprising at least one inelastic section mounted between the exterior surface and the interior surface; and
the inelastic section being terminally positioned adjacent to the at least one fastener, wherein the inelastic section is configured to positionally support the medical brace.

8. The system for covering and visually distinguishing an injured limb as claimed in claim 1 comprising:
the covering textile further comprising at least one vapor-permeable section; and
the vapor-permeable section being mounted between the exterior surface and the interior surface, wherein the at least one vapor-permeable section is positioned offset from the medical brace.

9. The system for covering and visually distinguishing an injured limb comprising:
a medical brace;
a covering textile;
at least one fastener;
at least one visual indicium;
the covering textile comprising an exterior surface and an interior surface;
the medical brace being enclosed within the covering textile;
the medical brace being positioned against the interior surface;
the covering textile being removably attached onto the medical brace by the at least one fastener;
the at least one visual indicium being mounted onto the exterior surface;
the at least one visual indicium comprising a retainer pocket, a placard insert, and a transparent section;
the retainer pocket being mounted to the exterior surface of the covering textile;
the placard insert being positioned into the retainer pocket; and
the transparent section being mounted to the retainer pocket and positioned over the placard insert.

10. The system for covering and visually distinguishing an injured limb as claimed in claim 9 comprising:
the at least one fastener being a first fastener and a second fastener;
the covering textile further composing a skirt edge extending between the exterior surface and the interior surface;
the first fastener being mounted to the interior surface of the covering textile adjacent to the skirt edge; and
the second fastener being mounted to the interior surface of the covering textile adjacent to the skirt edge, opposite the first fastener across the covering textile.

11. The system for covering and visually distinguishing an injured limb as claimed in claim 9 comprising:
each of the at least one fastener further comprising a length of webbing, an engagement device, and length-adjustment mechanism;
the length of webbing being terminally mounted to the covering textile;
the engagement device being terminally mounted to the length of webbing, opposite the covering textile; and
the length-adjustment mechanism being mounted to the length of webbing between the covering textile and the engagement device.

12. The system for covering and visually distinguishing an injured limb as claimed in claim 9 comprising:
at least one aperture; and
the at least one aperture traversing the covering textile between the interior surface and the exterior surface.

13. The system for covering and visually distinguishing an injured limb as claimed in claim 9 comprising:
the covering textile further comprising a first textile, a second textile, an interstitial layer, and an edge seam;
the edge seam being perimetrically mounted between the first textile and the second textile; and
the interstitial layer being delineated by the edge seam and positioned between the first textile and the second textile.

14. The system for covering and visually distinguishing an injured limb as claimed in claim 9 comprising:
the covering textile further comprising at least one inelastic section mounted between the exterior surface and the interior surface; and
the inelastic section being terminally positioned adjacent to the at least one fastener, wherein the inelastic section is configured to positionally support the medical brace.

15. The system for covering and visually distinguishing an injured limb as claimed in claim 9 comprising:
the covering textile further comprising at least one vapor-permeable section; and
the vapor-permeable section being mounted between the exterior surface and the interior surface, wherein the at least one vapor-permeable section is positioned offset from the medical brace.

* * * * *